United States Patent
Griffin et al.

(10) Patent No.: US 10,179,971 B2
(45) Date of Patent: Jan. 15, 2019

(54) METHOD FOR PROCESSING A CELLULOSIC FEEDSTOCK AT HIGH CONSISTENCY

(71) Applicant: IOGEN ENERGY CORPORATION, Ottawa (CA)

(72) Inventors: Robert Griffin, Ottawa (CA); Torbjorn van der Meulen, Ottawa (CA); Harold Neumann, North Augusta (CA); Robert Glenns, Ottawa (CA)

(73) Assignee: IOGEN ENERGY CORPORATION, Ontario (CA)

( * ) Notice: Subject to any disclaimer, the term of this patent is extended or adjusted under 35 U.S.C. 154(b) by 148 days.

(21) Appl. No.: 15/127,693

(22) PCT Filed: Mar. 20, 2015

(86) PCT No.: PCT/CA2015/050215
§ 371 (c)(1),
(2) Date: Sep. 20, 2016

(87) PCT Pub. No.: WO2015/139141
PCT Pub. Date: Sep. 24, 2015

(65) Prior Publication Data
US 2018/0179704 A1    Jun. 28, 2018

Related U.S. Application Data

(60) Provisional application No. 61/968,536, filed on Mar. 21, 2014.

(51) Int. Cl.
  *C12P 7/10* (2006.01)
  *C12P 7/14* (2006.01)
  (Continued)

(52) U.S. Cl.
  CPC .............. *D21C 1/10* (2013.01); *C12P 7/10* (2013.01); *C12P 7/14* (2013.01); *C12P 7/16* (2013.01);
  (Continued)

(58) Field of Classification Search
  None
  See application file for complete search history.

(56) References Cited

U.S. PATENT DOCUMENTS 3,992,754 A    11/1976  McCloskey et al.
5,562,777 A *  10/1996  Farone .................... C08B 15/02
                                                                127/1

(Continued)

FOREIGN PATENT DOCUMENTS

WO    2010/022511 A1    3/2010

OTHER PUBLICATIONS

B.N. Chakraborty et al., "Transfomration of Filamentous Fungi by Electroporation", Nucleic Acids Research, vol. 8, No. 22, p. 6737 (1990).
(Continued)

*Primary Examiner* — Richard C Ekstrom
(74) *Attorney, Agent, or Firm* — Venable LLP (57) ABSTRACT

Provided herein is a process for producing an alcohol from a sugar cane derived cellulosic feedstock comprising: subjecting the sugar cane derived cellulosic feedstock comprising bagasse, leaves, tops, or any combination thereof, to silica removal selected from processes comprising sieving, screening, washing, cyclone separation or any combination thereof. The bagasse, leaves or tops, or any combination thereof, from which at least a portion of the silica has been removed is treated in one or more processing stages to produce sugar, wherein the undissolved solids content of a slurry during said processing stages reaches a weight percent
(Continued)

US 10,179,971 B2
Page 2 of at least 15%. Thereafter the sugar is fermented with yeast or bacteria to produce the alcohol and the alcohol is concentrated and recovered.

27 Claims, 4 Drawing Sheets (51) Int. Cl.
| | |
|---|---|
| C12P 7/16 | (2006.01) |
| D21C 1/10 | (2006.01) |
| C12P 19/14 | (2006.01) |
| D21C 1/04 | (2006.01) |
| D21C 5/00 | (2006.01) |
| C12P 19/02 | (2006.01) |
| C13K 1/02 | (2006.01) |
| D21C 1/00 | (2006.01) |

(52) U.S. Cl.
CPC .............. *C12P 19/02* (2013.01); *C12P 19/14* (2013.01); *C13K 1/02* (2013.01); *D21C 1/00* (2013.01); *D21C 1/04* (2013.01); *D21C 5/005* (2013.01); *C12P 2201/00* (2013.01); *C12P 2203/00* (2013.01); *Y02E 50/16* (2013.01); *Y02E 50/17* (2013.01)

(56) References Cited

U.S. PATENT DOCUMENTS

| | | | | |
|---|---|---|---|---|
| 5,782,982 | A * | 7/1998 | Farone | C08B 15/02 127/1 |
| 7,901,511 | B2 | 3/2011 | Griffin et al. | |
| 8,328,947 | B2 | 12/2012 | Anand et al. | |
| 8,765,405 | B2 * | 7/2014 | Kurihara | B01D 61/022 210/600 |
| 9,127,325 | B2 * | 9/2015 | Nguyen | C12M 45/06 |
| 9,217,184 | B2 * | 12/2015 | Weydahl | C12P 7/10 |
| 9,476,066 | B2 * | 10/2016 | Foody | C10J 3/82 |
| 2005/0051287 | A1 * | 3/2005 | Chute | D21C 1/00 162/18 |
| 2010/0056774 | A1 | 3/2010 | Anand et al. | |
| 2012/0301939 | A1 | 11/2012 | Harvey et al. | |
| 2013/0071903 | A1 * | 3/2013 | Rowland | C13K 1/02 435/162 |
| 2014/0083918 | A1 | 3/2014 | Nguyen et al. | |
| 2014/0087432 | A1 | 3/2014 | Nguyen et al. | |
| 2014/0248676 | A1 * | 9/2014 | Griffin | D21C 11/0007 435/165 |

OTHER PUBLICATIONS

B.W. Hazell et al., "Rapid Transformation of High Cellulase-Producing Mutant Strains of Trichoderma Reesei by Microprojectile Bombardment", Letters in Applied Microbiology, vol. 30, pp. 282-286 (2000).

G. H. Goldman et al., "Transformation of Trichoderma Harzianum by High-Voltage Electric Pulse", Curr Genet, vol. 17, pp. 169-174 (1990).

P.L. Suominen et al., "High Frequency One-Step Gene Replacement in Trichoderma Reesei, II Effects of Deletions of Individual Cellulase Genes", Mol Gen Genet, vol. 241, pp. 523-530 (1993).

M.G. Steiger et al, "Transformation System for Hypocrea Jecorina (Trichoderma Reesei) That Favors Homologous Integration and Employs Reusable Bidirectionally Selectable Markers", Applied and Enviromental Microbiology, vol. 77, No. 1, pp. 114-121 (2011).

L. Canilha et al., "Bioconversion of Sugarcane Biomass into Ethanol: An Overview about Composition, Pretreatment Methods, Detoxification of Hydrolysates, Enzymatic Saccharification, and Ethanol Fermentation", Journal of Biomedicine and Biotechnology, Article ID 989572, vol. 2012, 15 pages (2012).

S.G. Allen et al., "Fractionation of Sugar Cane with Hot, Compressed, Liquid Water", Ind. Eng. Chem. Res., vol. 35, pp. 2709-2715 (1996).

"Bagasse Combustion in Sugar Mills", External Combustion Sources, section 1.8, pp. 1-8 (1996).

H.W. Bernhardt, "Dry Cleaning of Sugarcane—A Review", Proceedings of the South African Sugar Technologists Association, pp. 91-96 (1994).

C. Carrasco et al., "SO2-Catalyzed Steam Pretreatment and Fermentation of Enzymatically Hydrolyzed Sugarcane Bagasse", Enzyme and Microbial Technology, vol. 46, pp. 64-73 (2010).

M. Saska et al., "Pre-Treatment of Sugarcane Leaves and Bagasse Pith with Lime-Impregnation and Steam Explosion for Enzymatic Conversion to Fermentable Sugars", 28th Symposium on Biotechnology for Fuels and Chemicals, pp. 1-13 (2006).

"Feasibility of Improving Biomass Combustion Through Extraction of Nutrients", Cennatek Bioanalytical Services, 125 pages (2011).

D. Szczerbowski et al., "Assessment of Cane Straw as a Suitable Material for Bioconversion Through Steam Treatment and Enzymatic Hydrolysis", 14th International Biotechnology Symposium and Exhibition, abstract (2010).

V. Ferreira-Leitao, et al., "An Approach to the Utilisation of CO2 as Impregnating Agent in Steam Pretreatment of Sugar Cane Bagasse and Leaves for Ethanol Production", Biotechnology for Biofuels, vol. 3, No. 7, pp. 1-8 (2010).

S. Macrelli et al., "Techno-Economic Evaluation of 2nd Generation Bioethanol Production from Sugar Case Bagasse and Leaves Integrated with the Sugar-Based Ethanol Process", Biotechnology for Biofuels, vol. 5, No. 22, pp. 1-18 (2012).

S. H. Krishna et al., "Simultaneous Saccharification and Fermentation of Pretreated Sugar Cane Leaves to Ethanol", Process Biochemistry, vol. 33, No. 8, pp. 825-830 (1998).

S. J. Hassuani et al., eds., "Biomass Power Generation Sugar Cane Bagasse and Trash", pp. 1-3 and 24-27 (2005).

A. Bonomi, "Virtual Sugarcane Biorefinery: A Tool to Compare the Sustainability of Different Technological Alternatives", PASI 2011—Process Modeling and Optimization for Energy and Sustainability, 51 pages (2011).

International Search Report and Written Opinion for corresponding PCT/CA2015/050215, 10 pages (2015).

M. Saska et al., "Production of fuel ethanol from sugarcane bagasse and sugarcane trash," Congress on Sugar and Sugar Cane Derivatives, Havana, Cuba, 18 pages, Jun. 2006.

* cited by examiner

METHOD FOR PROCESSING A CELLULOSIC FEEDSTOCK AT HIGH CONSISTENCY

This application is a national stage application of PCT/CA2015/050215 having an international filing date of Mar. 20, 2015, which claims the benefit of U.S. Provisional Application No. 61/968,536 filed Mar. 21, 2014, each of which is incorporated by reference herein.

FIELD

The present disclosure relates to a method for processing cellulosic feedstock.

BACKGROUND

There is increasing interest in producing fuel ethanol or other fermentation products from cellulosic feedstocks. A particular feedstock of interest is cellulosic material remaining after sugar cane processing. The insoluble portion of sugar cane, which is known as bagasse, has a high polysaccharide content and could be suitable for conversion to ethanol or other fuels or chemicals. The leaves and tops of sugar cane can also serve as a source of sugar for conversion into such products.

One process proposed for producing a fermentation product, such as ethanol, from cellulosic materials derived from sugar cane is to carry out a pretreatment, followed by enzymatic hydrolysis of the cellulose to glucose. The pretreatment generally disrupts the fiber structure of the cellulosic feedstock and increases the surface area of the feedstock to make it accessible to cellulase enzymes. The pretreatment can be performed so that a high degree of hydrolysis of the xylan and only a small amount of conversion of cellulose to glucose occurs. The cellulose is hydrolyzed to glucose in a subsequent step that uses cellulase enzymes. Other pretreatment processes, such as certain alkali pretreatments, do not hydrolyze or result in limited xylan hydrolysis. Moreover, it is possible to hydrolyze both xylan and cellulose using more severe chemical treatment, such as concentrated acid hydrolysis.

Regardless of the method for producing fermentable sugar, the addition of water to the incoming feedstock to form a slurry is often carried out to facilitate the transportation and mechanical handling of the cellulosic feedstock. The slurry typically consists of cellulosic feedstock pieces or particles in water at a consistency of about 1 to about 10 wt % undissolved dry solids, as feedstock slurries can be more easily pumped when the dry solids content falls within this range.

However, for cellulosic conversion processes to be more economical, it would be desirable for them to operate at lower water content. The processing of feedstock of low water content has numerous advantages in various stages of the process, one of which is reduction in equipment size, which, in turn, reduces capital cost. Further benefits of low water content include reduced energy consumption including reductions in costs for pumping, heating, cooling and evaporating. Moreover, water usage costs can be reduced, which is especially advantageous in arid climates where water is at a premium.

Another problem associated with converting lignocellulosic feedstocks to ethanol and other fermentation products is the presence of ash in the in-coming feedstock, which contains inorganic salts, silica and other components. The presence of ash in lignocellulosic feedstocks, particularly inorganic salts such as potassium salts, is known to increase chemical consumption due to its buffering effect. It is known to remove ash from feedstocks such as wheat straw by leaching with an aqueous solution prior to chemical treatment as described in U.S. Pat. No. 7,901,511 (Griffin et al.). While leaching can reduce chemical demand, it may consume significant amounts of water. Thus, ash is often not removed from feedstocks such as wheat straw prior to processing due to the cost associated with its removal.

SUMMARY

Disclosed herein are processes for treating cellulosic feedstock, in particular cellulosic feedstocks derived from sugar cane.

According to a first aspect, there is provided a process for producing a fermentation product from a sugar cane derived cellulosic feedstock comprising: subjecting the sugar cane derived cellulosic feedstock comprising bagasse, leaves, tops, or a combination thereof, to silica removal selected from processes comprising separating at least silica from the feedstock by size or density differences; (ii) pretreating the bagasse, leaves or tops, or a combination thereof, from which at least a portion of the silica has been removed under pressure to produce a pretreated feedstock; (iii) at least partially de-pressurizing the pretreated feedstock comprising passing the pretreated feedstock through an orifice, thereby producing a depressurized, pretreated feedstock; (iv) hydrolyzing the depressurized, pretreated feedstock with cellulase enzymes to produce glucose; and (v) fermenting the glucose to produce the fermentation product.

According to embodiments, the orifice may be formed within a valve. The valve may be a blow valve.

In a further embodiment, the sugar cane derived cellulosic feedstock may be at least partially de-watered after step (i) and before the step of pretreating. The pretreating may comprise addition of an acid.

In addition to removing silica, step (i) may comprise removing inorganic salt, iron and alumina from the sugar cane derived cellulosic feedstock.

According to a further aspect, there is provided a process for producing an alcohol from a sugar cane derived cellulosic feedstock comprising: (i) subjecting the sugar cane derived cellulosic feedstock comprising bagasse, leaves, tops, or a combination thereof, to silica removal selected from processes comprising sieving, screening, washing, cyclone separation or any combination thereof, thereby removing at least silica therefrom; (ii) treating the bagasse, leaves or tops, or any combination thereof, from which at least a portion of the silica has been removed, in one or more processing stages to produce sugar, wherein the undissolved solids content of a slurry during said processing stages reaches a weight percent of at least 15%; (iii) fermenting the sugar to produce the alcohol with yeast or bacteria; and (iv) concentrating and recovering the alcohol.

According to another aspect, there is provided a process for producing a fermentation product from a sugar cane derived cellulosic feedstock comprising: (i) subjecting the sugar cane derived cellulosic feedstock comprising bagasse, leaves, tops, or a combination thereof, to silica removal selected from processes comprising sieving, screening, washing, cyclone separation or any combination thereof, thereby removing at least silica therefrom; (ii) treating the bagasse, leaves, tops, or any combination thereof, from which at least a portion of the silica has been removed, in one or more processing stages to produce sugar, wherein the undissolved solids content of a slurry during said processing stages is between 12 and 35 weight percent; (iii) fermenting the sugar to the fermentation product with yeast or bacteria; and (iv) recovering the fermentation product. According to various embodiments, the one or more processing stages may comprise high consistency process equipment that comprises a dewatering device. The dewatering device may be a screw press or plug screw.

The one or more processing stages to produce fermentable sugar may comprise pretreatment. The silica may be removed upstream of pretreatment.

The bagasse, leaves, tops or any combination thereof, may have an ash content of between 0.5 wt % and about 18 wt %. The ash content may be between 5 wt % and 18 wt %.

The bagasse, leaves, tops or any combination thereof may be subjected to dry sieving. Optionally, the bagasse, leaves, tops or any combination thereof may be dried prior to dry sieving.

In a further embodiment, the bagasse, leaves, tops or any combination thereof may be subjected to wet processing comprising removing at least silica by settling or by using at least one hydrocyclone.

According to a further embodiment, at least 20 weight percent of the silica from the bagasse, tops, leaves or any combination thereof may be removed prior to the step of treating (w/w).

In a further embodiment, at least 40 weight percent of the silica from the bagasse, tops, leaves or any combination thereof may be removed prior to the step of treating.

According to a further embodiment, the one or more processing stages comprise soaking the bagasse, tops, leaves or any combination thereof in an aqueous solution.

The aqueous solution may comprise a pretreatment chemical.

In further embodiments, the undissolved solids content of a slurry during the processing stages may reach a weight percent of at least 20% (w/w).

In additional embodiments, the one or more processing stages may comprise a step of pretreatment to produce pretreated feedstock and hydrolysis of cellulose contained in the pretreated feedstock with cellulase enzymes to produce the sugar.

According to a further aspect, there is provided a process for producing a fermentation product from a sugar cane derived cellulosic feedstock comprising: (i) subjecting the sugar cane derived cellulosic feedstock comprising bagasse, leaves, tops, or a combination thereof, to silica removal selected from processes comprising sieving, screening, washing, cyclone separation or any combination thereof, thereby removing at least silica therefrom; (ii) treating the bagasse, leaves or tops, or any combination thereof, from which at least a portion of the silica has been removed, in one or more processing stages to produce sugar, wherein the undissolved solids content of a slurry fed to or formed during said one or more processing stages reaches a weight percent of at least 15%, and the processing stages comprise feeding a process stream to equipment susceptible to erosion by silica originating from the sugar can derived feedstock, the equipment selected from a dewatering device, a heating chamber, a valve or a combination thereof; and (iii) fermenting the sugar to produce the fermentation product.

According to one embodiment, the equipment may be a dewatering device, such as a plug screw feeder and a screw press. According to a further embodiment, the equipment may be a steam mixing device. In another embodiment, the equipment may be a blow valve.

According to a further aspect, there is provided a process for producing a fermentation product from a sugar cane derived cellulosic feedstock comprising: (i) subjecting the sugar cane derived cellulosic feedstock comprising bagasse, leaves, tops, or a combination thereof, to silica removal selected from processes comprising sieving, screening, washing, cyclone separation or a combination thereof, thereby removing at least silica therefrom; (ii) producing a slurry of the sugar cane derived cellulosic feedstock before, after or during step (i); (iii) dewatering the slurry with at least one dewatering device to produce an at least partially dewatered material; (iv) pretreating the dewatered material, from which at least a portion of the silica has been removed in step (i) under pressure to produce a pretreated feedstock; (iii) at least partially de-pressurizing the pretreated feedstock comprising passing the pretreated feedstock through an orifice, thereby producing a depressurized, pretreated feedstock; (iv) hydrolyzing the depressurized, pretreated feedstock with cellulase enzymes to produce glucose; and (v) fermenting the glucose to produce the fermentation product.

DETAILED DESCRIPTION

The headings provided are not meant to be limiting of the various embodiments described herein. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

As mentioned, sugar cane bagasse, tops, leaves, or any combination of these materials, are currently of interest for second generation biofuel production. However, process streams derived from these materials are often difficult to handle. Embodiments are based on the recognition that erosion in process equipment is particularly problematic, such as equipment used when operating at high consistency, with cellulosic feedstocks derived from sugar cane due to the high level of silica introduced to the process from the incoming feedstock. Erosion damage to equipment exposed to process streams with high levels of silica can be costly as it necessitates frequent repair, costly replacement of equipment or downtime.

Furthermore, it has been found that the characteristics of the silica component of ash in sugar cane derived cellulosic feedstock vary considerably from those of silica present in other cellulosic feedstocks such as wheat straw. As described herein, these differences may contribute to increased wear on equipment observed when using sugar cane derived cellulosic material as a feedstock. An example of such equipment prone to erosion damage is a dewatering device, a heating chamber, a pump or a valve. The dewatering device may include a plug screw feeder or a pressurized screw press. The heating chamber may include a steam mixer. Pumps that are prone to erosion include positive displacement pumps, such as progressive cavity pumps and centrifugal pumps. The valve may be a device through which feedstock passes through after it has been pretreated, such as a blow valve.

The disclosed embodiments involve removing at least silica prior to processing sugar cane bagasse, leaves and/or tops. Removing at least silica from such sugar cane derived cellulosic feedstock may reduce erosion on equipment when processing material containing this feedstock or feedstock derived therefrom. By removing silica in an upstream stage of the process, most advantageously prior to pretreatment, erosion damage may be reduced, thereby resulting in significant savings in operating and capital costs.

Feedstock

The starting material for use in the process is sugar cane derived cellulosic feedstock comprising bagasse, tops, leaves, or any combination thereof. Bagasse is material that remains after pressing sugar cane stalks to obtain sugar juice. Sugar cane leaves include any green leaves and/or dry leaves of a sugar cane plant. The tops may include the part of the cane plant between the top end and the last stalk node. The tops and/or leaves of the sugar cane may be separated from the sugar cane stalk at a sugar cane mill or in the fields where the plants are grown.

The sugar cane derived cellulosic feedstock including bagasse, leaves, and/or tops may comprise cellulose, hemicellulose and lignin in an amount greater than about 20%, more preferably greater than about 30%, more preferably greater than about 40% (w/w). For example, the bagasse, leaves or tops may comprise from about 15% to about 50% (w/w) cellulose, or any amount therebetween. Such feedstocks comprise hemicellulose, including xylan, arabinan, mannan and galactan. Furthermore, the feedstock may comprise lignin in an amount greater than about 10%, more typically in an amount greater than about 15% (w/w).

The sugar cane derived cellulosic feedstock may contain greater than 0.5 wt % ash (w/w), or more typically greater than 1 wt %, 3 wt % or 5 wt % ash (w/w). The ash includes, but is not limited to, silica sand, also referred to herein as "silica", salts of potassium, calcium and sodium. Iron and alumina may be present in the ash as well. The salts may exist as carbonate, phosphate, chloride or other common salt forms. Magnesium and other minerals may be present as well depending on the source of the feedstock. In some embodiments, the ash content of the sugar cane derived cellulosic feedstock is between about 0.5 wt % and about 18 wt %, between about 3 wt % and about 18 wt %, or between about 5 wt % and about 18 wt %. The ash content is determined according to Example 1.

Optionally, the sugar cane derived cellulosic feedstock is subjected to size reduction by methods including, but not limited to, milling, grinding, agitation, shredding, compression/expansion, or other types of mechanical action. The feedstock may have particles of a length of about 1/16 to about 8 inches, 1/16 to 5 inches, or any amount therebetween. However, it should be understood that the sugar cane derived cellulosic feedstock need not be subjected to size reduction.

Silica Removal

The embodiments comprise subjecting the sugar cane derived cellulosic feedstock comprising bagasse, leaves and/or tops to a silica removal process. It should be appreciated that at least a portion of the silica is removed from the sugar cane derived feedstock. For example, at least 50 wt % of the silica (w/w) may be removed from the native feedstock. Further, a silica removal process may additionally remove other components of ash in the feedstock including, but not limited to, inorganic salts, iron and/or alumina. The silica removal may include dry or wet processing methods.

In a dry process the sugar cane derived cellulosic feedstock may be subjected to sieving and/or screening by known techniques. Dry sieving or screening processes do not include addition of liquid. Prior to sieving or screening, the feedstock may be dried as this may improve silica removal.

Wet processing may include the addition of water. Wet processing may involve the use of one or more cyclone separators. Wet processing may alternatively or in addition, rely on settling of at least silica in one or more vessels. This may include using a tank to allow at least silica to settle from the feedstock, optionally combined with one or more washing stages upstream of settling. A non-limiting example of a wet processing technique involves using a vessel to remove heavy particles by settling and cyclone separation to remove finer particles. A further example includes using agitated tanks that are conical in shape.

The processes for silica removal can also be characterized according to differences in physical properties between the silica and feedstock to effect separation. That is, the processes may be characterized by a separation based on size differences between the silica and the sugar cane derived feedstock or differences in density. Separation processes based on separation by size include sieving or screening, while separation processes based on density, include, but are not limited to settling and cyclone separating.

The level of ash removed from the sugar cane bagasse, leaves and/or tops may be at least 30 wt %, at least 40 wt %, at least 50 wt %, at least 60 wt % or at least 70 wt % relative to the incoming feedstock (w/w).

Production of Sugar at High Consistency

After silica removal, the sugar cane derived cellulosic feedstock may be subjected to one or more processing stages to produce sugar. The processing stages may be conducted at a consistency of between 12 and 35 wt %, 14 and 30 wt % or any range therebetween. According to certain embodiments, the undissolved solids content of a slurry during said processing stages reaches a weight percent of at least 15, 18, 20, 22, 24, 26, 28 or 30 wt %.

The consistency of a slurry or process stream is measured as the undissolved solids content ("UDS") as set out in Example 2.

A variety of processing stages can be carried out to produce sugar from the bagasse, leaves and/or tops at high consistency. Such processing may include pretreating the sugar cane derived cellulosic feedstock to disrupt fiber structure and improve accessibility of cellulose to a subsequent enzymatic hydrolysis which hydrolyzes cellulose to glucose. Examples of these processing stages are described in turn below.

(a) Processing Prior to Pretreatment

The processing stages may include one or more steps carried out to prepare the sugar cane derived cellulosic feedstock for pretreatment. Examples of such steps include (i) heat treatment, (ii) chemical treatment, such as swelling or soaking, or a combination thereof.

Heat treatment may include the use of heat to treat the feedstock at a temperature of above 80° C. This can involve a step of steaming or a soaking step with application of heat. The feedstock may be heated with steam using commercially available mixing devices designed for introducing steam and optionally chemical through spray nozzles.

The feedstock may be soaked in an aqueous solution including water, or a solution comprising pretreatment chemical. A benefit of soaking the feedstock prior to pretreatment with a solution comprising pretreatment chemical is that it can ensure uniform impregnation of the feedstock with the pretreatment chemical, which in turn helps achieve even cooking in the subsequent pretreatment. Uniform impregnation ensures that some feedstock is not overcooked and degraded due to the high localized concentration of the pretreatment chemical, while other feedstock is not undercooked, resulting in low xylose yield and difficult cellulose hydrolysis. Undercooking or overcooking of cellulosic feedstock can be particularly problematic when the pretreatment is conducted under medium or high solids consistency because the non-uniformity of the concentration of the pretreatment chemical and the temperature are more pronounced.

In order to achieve the target consistencies set out previously, the process may comprise one or more steps of dewatering a feedstock slurry prior to pretreatment, although it is possible to eliminate dewatering if the feedstock solids content is already within the target range. The dewatering may increase the consistency of the feedstock slurry to above 15 wt %, 18 wt %, 20 wt %, 22 wt %, 24 wt %, 26 wt %, 28%, 30 wt %, 32 wt %, 34 wt % or 36 wt %. Examples of ranges include 15 to 36 wt % undissolved solids or 18 to 32 wt % undissolved solids. The dewatering may involve removing water under pressure from the feedstock, or at atmospheric pressure, as discussed below.

One method for reducing water content is to dewater a sugar cane derived cellulosic feedstock slurry to form a compacted plug of material prior to carrying out pretreatment in a downstream reactor (see WO 2010/022511, which is incorporated herein by reference). Plugs of feedstock can be produced by various devices, such as plug screw feeders, pressurized screw presses, co-axial piston screw feeders or modular screw devices.

When producing a plug of material, the water content of the feedstock is reduced so that the solids content is high enough for plug formation to occur. Dewatering can take place within a plug formation device itself or dewatering and plug formation can be carried out in separate pieces of equipment. There are a variety of known devices that can be utilized to dewater the feedstock prior to plug formation. Examples include drainers, filtration devices, screens, screw presses, extruders or a combination thereof.

Without being limiting, a plug formation device incorporating a dewatering section suitable for use in the disclosed embodiments may be a pressurized screw press or a plug screw feeder, as described in WO 2010/022511, which is incorporated herein by reference. Water expressed from the feedstock by the dewatering step may be reused in the process, such as for slurrying and/or soaking the incoming feedstock.

If the sugar cane derived cellulosic feedstock is subjected to dewatering under pressure, the pressure increase may be caused by one or more high pressure pumps. The pump or other feeding device increases the pressure of the feedstock prior to dewatering. Alternatively, the feedstock subjected to dewatering may be at atmospheric pressure or at a pressure below about 45 psia.

There may be an optional step of pre-draining the feedstock in order to drain out aqueous solution from the feedstock slurry at atmospheric pressure or higher. This pre-drained feedstock slurry can then be subjected to further dewatering.

The plug of sugar cane derived cellulosic feedstock may have an undissolved dry solids content of between about 20 and 50 wt %, between about 20 and 40 wt % or between 20 and 35 wt %. As discussed, by removing all, or a portion, of the silica from the feedstock, the process equipment may be less prone to erosion that is particularly problematic at high consistencies.

After plug formation, the cellulosic feedstock plug or segments thereof may be disaggregated into particles and heated with steam using a device as set forth in co-pending and co-owned U.S. Publication No. 2013/0071903.

(b) Pretreatment

After the treatment steps to increase the feedstock consistency, the feedstock may be subjected to pretreatment. The pretreatment is operated at an undissolved solids content range of between 12 wt % and 35 wt %, or any range therebetween.

Pretreatment may be with heat, mechanical processing, addition of one or more chemicals, biocatalysts, or combinations thereof. After pretreatment, between 30 and 100 wt % of the xylan may be hydrolyzed, although there may be limited xylan hydrolysis during some pretreatments. After pretreatment, between 10 and 100 wt % of the lignin may remain insoluble. Non-limiting examples of pretreatment include acid pretreatment, alkali pretreatment and hydrothermal pretreatment, each of which are discussed in turn below. An acid pretreatment may be carried out at a maximum temperature of about 120° C. to about 280° C. The time that the feedstock is held at this temperature may be about 6 seconds to about 2 hours. The acid pretreatment produces a composition comprising an acid pretreated feedstock. Sugars produced by the hydrolysis of hemicellulose during acid pretreatment are generally present in the composition and may include xylose, glucose, arabinose, mannose, galactose or a combination thereof. Organic acids may be present in the composition as well and may include acetic acid, galacturonic acid, formic acid, lactic acid, glucuronic acid or a combination thereof. Many cellulosic feedstocks contain hemicellulose with acetyl groups attached to xylan. Pretreatment processes liberate acetic acid from the acetyl groups.

Examples of suitable alkali pretreatment processes include ammonia fiber expansion (AFEX) or dilute ammonia pretreatment. According to the AFEX process, the cellulosic biomass is contacted with ammonia or ammonium hydroxide, which is typically concentrated, in a pressure vessel. The contact is maintained for a sufficient time to enable the ammonia or ammonium hydroxide to swell the cellulose fibers. The pressure is then rapidly reduced which allows the ammonia to flash or boil and explode the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

A hydrothermal pretreatment may be carried out without the addition of pretreatment chemical, with the application of heat. An example of a suitable temperature for hydrothermal pretreatment is between about 80° C. and about 260° C., or between about 100° C. and about 210° C. Without being limiting, equipment that can be used to carry out hydrothermal pretreatment is an extruder.

Various types of reactors may be used to pretreat the feedstock including two or more reactors, arranged in series or parallel. According to one embodiment, the reactor is a vertical reactor, which may be either an upflow or a downflow vertical reactor. In another embodiment, the reactor is a horizontal or inclined reactor. The reactor may be equipped with an internal mechanism, such as a screw, conveyor, scraper or similar mechanism, for conveying the lignocellulosic feedstock therethrough and/or to aid in discharging the reactor.

Chemical for pretreating the feedstock may be added to the feedstock during a soaking process carried out prior to dewatering, prior to plug formation, into the heating chamber, into the plug formation device, into the reactor, or a combination thereof.

Pressure in the reactor may be between about 90 psia and about 680 psia and any pressure therebetween or between 100 psia and 650 psia. The pressure of the pretreated, pressurized feedstock may then be reduced in one or more stages. In an embodiment, the depressurization involves passing the pressurized, pretreated feedstock through an orifice. The orifice may be between 1 and 8 inches in diameter or between 1.5 and 7 inches in diameter. As set forth in the examples, passage of a pressurized sugar cane derived feedstock slurry through an orifice, such as an orifice formed in a valve, at high velocity may cause erosion due to the presence of silica in the sugar cane derived feedstock. Erosion damage from silica found in the sugar cane bagasse was found to be more erosive than silica from wheat straw. Thus, removing sugar cane bagasse silica upstream of the depressurization may reduce equipment wear and decrease downtime associated with replacing worn equipment.

(c) Enzymatic Hydrolysis

The pretreated feedstock contains cellulose, which may be subjected to cellulose hydrolysis with cellulase enzymes. By the term "cellulase enzymes", "cellulase", or "enzymes", it is meant enzymes that catalyze the hydrolysis of cellulose to products such as glucose, cellobiose, and other cello-oligosaccharides. Cellulase is a generic term denoting a multienzyme mixture comprising exo-cellobiohydrolases (CBH), endoglucanases (EG) and β-glucosidases (βG) that can be produced by a number of plants and microorganisms. The process of the disclosed embodiments may be carried out with any type of cellulase enzymes, regardless of their source.

Optionally, prior to the enzymatic hydrolysis, the sugars arising from pretreatment are separated from unhydrolyzed feedstock components in the pretreated feedstock slurry. Processes for carrying out the separation include, but are not limited to, filtration, centrifugation, washing or other known processes for removing fiber solids or suspended solids. The aqueous sugar stream may then be concentrated, for example, by evaporation, with membranes, or the like. Any trace solids are typically removed by microfiltration.

In one embodiment, the aqueous sugar stream separated from the fiber solids is fermented to produce an alcohol by a yeast or bacterium. The alcohol may be ethanol or butanol or a sugar alcohol selected from xylitol, arbitol, erythritol, mannitol and galactitol. Preferably, the sugar alcohol is xylitol.

A temperature in the range of about 45° C. to about 55° C., or any temperature therebetween, may be suitable for most cellulase enzymes, although the temperature may be higher for thermophilic cellulase enzymes. An appropriate cellulase dosage may be about 1.0 to about 40.0 mg of protein per gram of cellulose, or any amount therebetween. The protein concentration can be measured according to Smith et al., 1985, Anal Biochem. 150(1):76-85; which is incorporated herein by reference. A preferred cellulase dosage is about 1 to 15 mg per gram cellulose.

The enzymatic hydrolysis of the cellulose may be carried out for about 24 hours to about 250 hours, or any amount of time therebetween, depending on the degree of conversion desired. The slurry thus produced may be an aqueous solution comprising glucose, xylose, other sugars, lignin and other unconverted, suspended solids.

Fermenting the Sugar

After enzymatic hydrolysis, the sugars may be separated from the suspended solids and fermented to produce fermentation products, including, but not limited to ethanol or butanol by yeast or bacterium or sugar alcohols. If ethanol is produced, the fermentation may be carried out with a yeast, including, but not limited to *Saccharomyces cerevisiae*.

The dissolved sugars that are subjected to the fermentation may include not only the glucose released during cellulose hydrolysis, but also sugars arising from a pretreatment, namely xylose, glucose, arabinose, mannose, galactose or a combination thereof. These sugars may be fermented together with the glucose produced by cellulose hydrolysis or they may be fed to a separate fermentation. In one embodiment, such sugars are converted to ethanol, along with the glucose from the cellulose hydrolysis, by a *Saccharomyces cerevisiae* yeast strain having the capability of converting both glucose and xylose to ethanol. The *Saccharomyces cerevisiae* strain may be genetically modified so that it is capable of producing this valuable byproduct (see, for example, U.S. Pat. No. 5,789,210, which is incorporated herein by reference), although it has been reported that some *Saccharomyces cerevisiae* yeast strains are naturally capable of converting xylose to ethanol.

Recovering the Fermentation Product

If ethanol or butanol is the fermentation product, the recovery may be carried out by distillation, typically with further concentration of the product by molecular sieves or membrane extraction.

The fermentation beer that is sent to distillation is a dilute alcohol solution. The fermentation beer may comprise lignin solids that are part of an undissolved solids content of the beer, including unconverted cellulose, and any components added during the fermentation to support growth of the microorganisms.

Microorganisms may be present during the distillation depending upon whether or not they are recycled during fermentation. The broth may be degassed to remove carbon dioxide and then pumped through one or more distillation columns to separate the alcohol from the other components in the broth. The mode of operation of the distillation system may depend on whether the alcohol has a lower or a higher boiling point than water. Most often, the alcohol has a lower boiling point than water, as is the case when ethanol is distilled.

In those embodiments in which ethanol is concentrated, the column(s) in the distillation unit may be operated in a continuous mode, although it should be understood that batch processes may also be used. Heat for the distillation process may be introduced at one or more points either by direct steam injection or indirectly via heat exchangers. The distillation unit may contain one or more separate beer and rectifying columns, in which case dilute beer may be sent to the beer column where it is partially concentrated. From the beer column, the vapour may go to a rectification column for further purification. Alternatively, a distillation column may be employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

When the alcohol has a higher boiling point than water, such as butanol, the distillation may be run to remove the water and other volatile compounds from the alcohol. The water vapor exits the top of the distillation column and is known as the "overhead stream".

A process stream remaining after distillation and containing solids, referred to herein as "still bottoms" or as a "still bottoms stream", may be withdrawn from the bottom of one or more of the column(s) of a distillation unit.

While particular embodiments have been described in the foregoing, it is to be understood that other embodiments are possible and are intended to be included herein. It will be clear to any person skilled in the art that modifications of and adjustments to the foregoing embodiments, not shown, are possible.

EXAMPLES

Example 1

Determination of the Ash Content of a Sugar Cane Derived Cellulosic Feedstock

The amount of ash is expressed as the percentage of residue remaining after dry oxidation at 575° C. in accordance with NREL Technical Report NREL/TP-510-42622, January 2008, which is incorporated herein by reference. The results are reported relative to a 105° C. oven dried sample (dried overnight).

In order to determine the ash content, a crucible is first heated without any sample in a muffle furnace for 4 hours at 575±25° C., cooled and then weighed. After heating, the crucible is cooled and then dried to constant weight, which is defined as less than a ±3 mg change in the weight of the crucible upon one hour of re-heating the crucible at 575±25° C.

The sample analyzed is a 105° C. oven dried specimen. The weight of the oven dried sample is recorded after drying at 105° C. overnight in an oven and this weight is referred to as "oven dried weight" or "ODW". The dried, weighed sample is placed in the crucible and ashed to constant weight in a muffle furnace set to 575±25° C. The crucible and ash are weighed subsequent to ashing and the percentage ash is determined on an ODW basis. The ash is quantified by determining, as a percent, the number of grams of ash per gram of oven dried sample.

Example 2

Determination of the Undissolved Solids Concentration in a Sugar Cane Derived Cellulosic Feedstock Slurry The determination of the undissolved dry solids (UDS) content in a slurry is carried out as follows.

A fixed amount of slurry is dispensed into a plastic weigh dish and the slurry weight is recorded accurately using an analytical scale. A 1.6 µm filter paper circle, appropriately sized for a Buchner funnel, is placed in an aluminum weighing tin and the combined weight of the tin and filter paper is recorded. After transferring the pre-weighed filter paper to the Buchner funnel, the pre-weighed slurry is passed through the filter paper to isolate the solids. Small volumes of de-ionized water are used to ensure that the solids are quantitatively transferred from the weigh dish to the Buchner funnel. The solids are then washed using excess deionized water, after which the washed sample and filter paper are transferred into the pre-weighed aluminum tin. Care should be taken to ensure the solids are quantitatively transferred. After drying the aluminum tin in a 105° C. oven overnight, the contents are weighed accurately and the UDS content is quantified by determining, as a percent or ratio, the number of grams of dry solids per gram of slurry.

Example 3

Processing Sugar Cane Derived Cellulosic Feedstock Under Low Water Conditions

Figure 1:
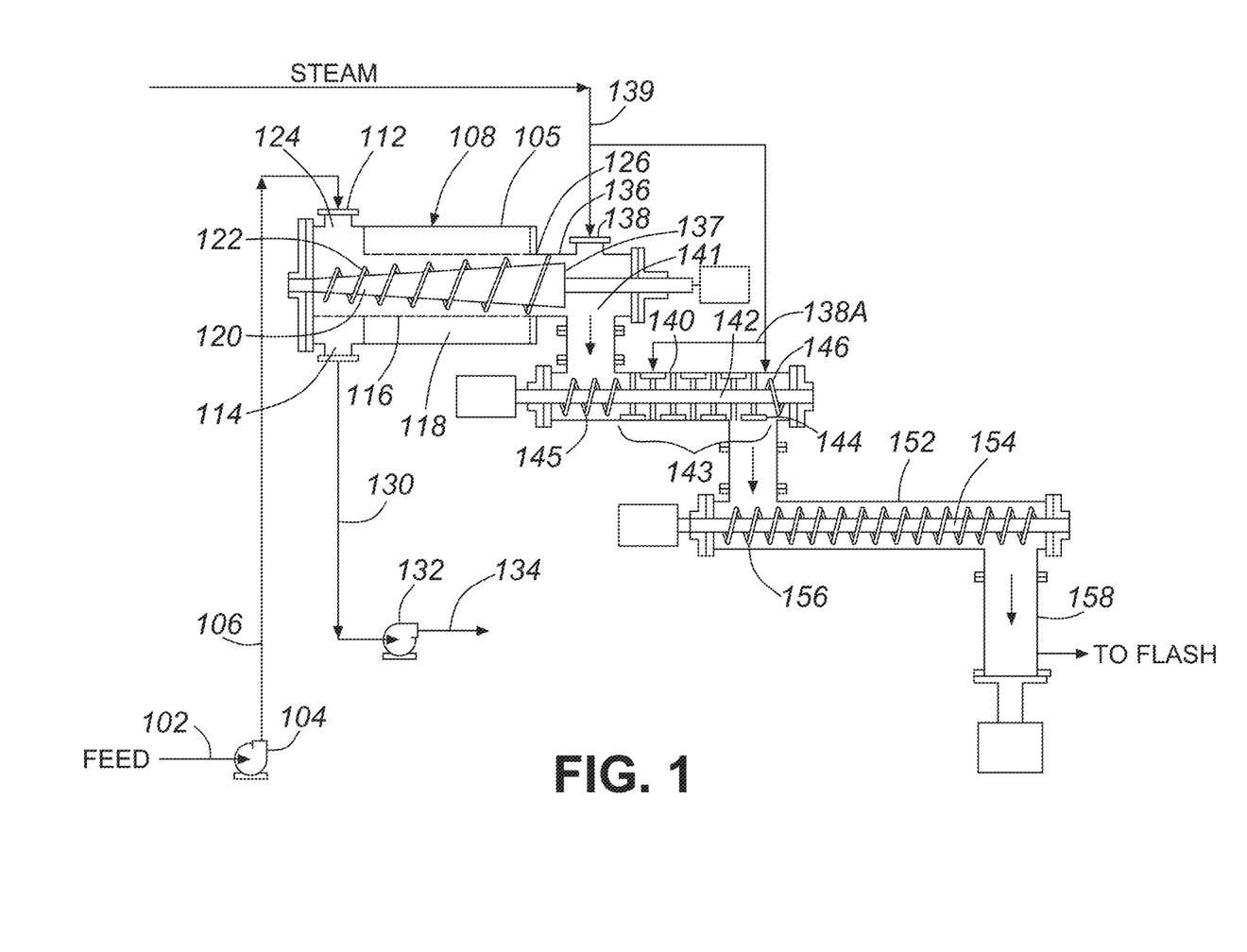
FIG. 1 is a pretreatment system in which sugar cane derived cellulosic material can be pretreated after silica removal.

With reference to FIG. 1, a slurry of sugar cane derived cellulosic feedstock having a consistency of about 1% to about 10% (w/w), preferably about 3% to about 5% (w/w) in slurry line 102 is pumped by means of pump 104 through in-feed line 106 into pressurized dewatering screw press indicated by general reference number 108. Pressurized dewatering screw press 108 comprises a solid shell 105 having a feedstock inlet port 112 and a pressate port 114. In-feed line 106 feeds sugar cane derived feedstock slurry into the dewatering screw press 108 through the feedstock inlet port 112 at a pressure of, e.g., about 70 psia to about 900 psia. The pressure may be determined by measuring the pressure with a pressure sensor (not shown) located at feedstock inlet port 112.

A screen 116 is disposed within shell 105 to provide an outer space 118 between the screen and the inner circumference of shell 105. A screw 120 is concentrically and rotatably mounted within the screen 116. Flights 122 of the screw 120 are of generally constant outside diameter and attached to a screw shaft with a core diameter that increases from the inlet end 124 to the outlet end 126 of the pressurized dewatering screw press 108.

Water and any other liquids, including dissolved solids, which have been expressed from the sugar cane derived feedstock slurry are withdrawn into the space 118, which serves as a collection chamber for the withdrawn water. The space 118 is connected through the pressate port 114 to a turbine 132 that draws withdrawn water through a pressate line 130. The withdrawn water, or pressate, may then be sent to a pressate return slurry make-up system (not shown) via line 134.

The partially dewatered sugar cane derived feedstock exits the dewatering and plug formation zone of the screw press 108 at the outlet end 126. The ratio of the weight of water to dry sugar cane derived feedstock solids in the partially dewatered sugar cane derived feedstock may be in the range of about 1.5:1 (67 wt % UDS) to about 4:1 (20 wt % UDS) exiting the dewatering and plug formation zone. The weight ratio of water to dry sugar cane derived feedstock solids in the dewatered sugar cane derived feedstock or the percent undissolved dry solids is determined by collecting a sample of the feedstock from, e.g., outlet end 126 of the screw press 108, and determining the weight ratio or weight % UDS in the sample by the method described in Example 2 above.

The outlet end 126 of the pressurized screw press 108 is operatively connected to a plug zone 136. A plug of the partially dewatered sugar cane derived feedstock is forced through the plug zone 136 and is discharged at plug outlet 137. There may also be a restraining device (not shown) at the plug outlet 137.

A steam inlet port 138 and/or ports 138A are supplied by a source of steam via steam inlet line 139. The plug of partially dewatered feedstock, which contains water in the range of about 0.5 to about 5 times the weight of the dry feedstock solids, is fed into a high shear heating chamber (also referred to as a steam mixer) 140 via a feed chamber 141.

In the high shear heating chamber 140, the feedstock plug, or segments thereof, is disintegrated into particles, which are heated by direct steam contact via steam introduced through line 139 and/or ports 138A. Steam may also be introduced into the body of the heating chamber 140. As mentioned previously, the plug may break into segments as it is discharged from the pressurized screw press 108, or as it is fed into other devices positioned downstream of the screw press 108.

The heating chamber 140 is a cylindrical, horizontally-oriented device having a concentric, rotatable shaft 142 mounted co-axially in the chamber. The concentric shaft 142 comprises a plurality of disintegrating elements 143 mounted on its mid-region and that project radially therefrom. Some disintegrating elements comprise a distal end 144 that is "T-shaped" for sweeping the inner surface of the chamber 140, as described below. The inlet region of the shaft 142 comprises an inlet auger 145 for conveying the plug, or segments thereof, into the mid-region of the chamber. In addition, an outlet auger 146, with opposite pitch, is provided in an outlet region of the shaft 142 for discharging heated, disintegrated feedstock produced in the heating chamber 140 into a pretreatment reactor 152.

Shearing action is imparted to the feedstock plug or segments thereof, in the heating chamber 140 by the plurality of disintegrating elements 143. During disintegration, the feedstock plug or segments thereof are broken down into small particles.

The heated, disintegrated feedstock is discharged from the heating chamber 140 into the pretreatment reactor 152, which comprises a cylindrical, horizontally-oriented vessel within which is mounted a screw conveyor 154 having flights 156. The pretreatment reactor 152 operates at a pressure of about 90 psia to about 680 psia, a pH of about 0.5 to about 3.0 and a temperature of about 160° C. to about 260° C. The sugar cane derived feedstock is treated in the reactor for a time of about 10 to about 600 seconds. The desired pH in the reactor 152 may be obtained by adding acid to the sugar cane derived feedstock prior to the inlet port 112 of the pressurized screw press.

A discharge device 158 discharges the pretreated feedstock from the pretreatment reactor 152. Subsequently, the pretreated feedstock is flashed in a flash vessel or vessels (not shown) to cool it before enzymatic hydrolysis.

Sugar cane derived feedstock containing ash rich in silica was found to cause excessive material loss in process areas prone to erosion. The areas where erosion occurred were in the pump 104, the pressurized screw press 108, the high shear heating chamber 140 and a blow valve located in the discharge device 158 of the pretreatment reactor 152.

Example 4

Silica Removal from Sugar Cane Derived Feedstock Reduces Equipment Wear

Studies were conducted on equipment wear by determining material loss in a process area prone to erosion in the high consistency pretreatment system described in Example 3 with reference to FIG. 1. In this example, damage to a blow valve component located in the discharge device 158 was examined with a sugar cane derived cellulosic feedstock with and without ash removal and compared to damage caused by wheat straw having a similar silica content. The sugar cane derived feedstock in this example was sugar cane bagasse obtained from Brazil.

Silica was removed from feedstock using a dry ash removal method, referred to herein as "de-ashing", to produce de-ashed feedstock. The wheat straw had been hammer milled in a hammer mill with ¾ inch screens and was not subjected to ash removal.

The as-received bagasse, de-ashed bagasse and wheat straw were pretreated in the system described in FIG. 1. The impact of erosion on the blow valve in the discharge device 158 was examined by measuring material loss of blow valve components as a function of time in g/kg. In particular, seat retainer ring material loss of the blow valve was examined. The valve seat retainer ring is a ring made of stainless steel that holds a ceramic valve seat in place by a screw fit. The valve seat is a component of the valve which a plug contacts when the valve is in a closed position. The weight of the valve seat retainer ring was measured at various time points and the loss was measured in grams per original kilograms of material before exposure to the feedstock slurry containing silica.

Figure 2:
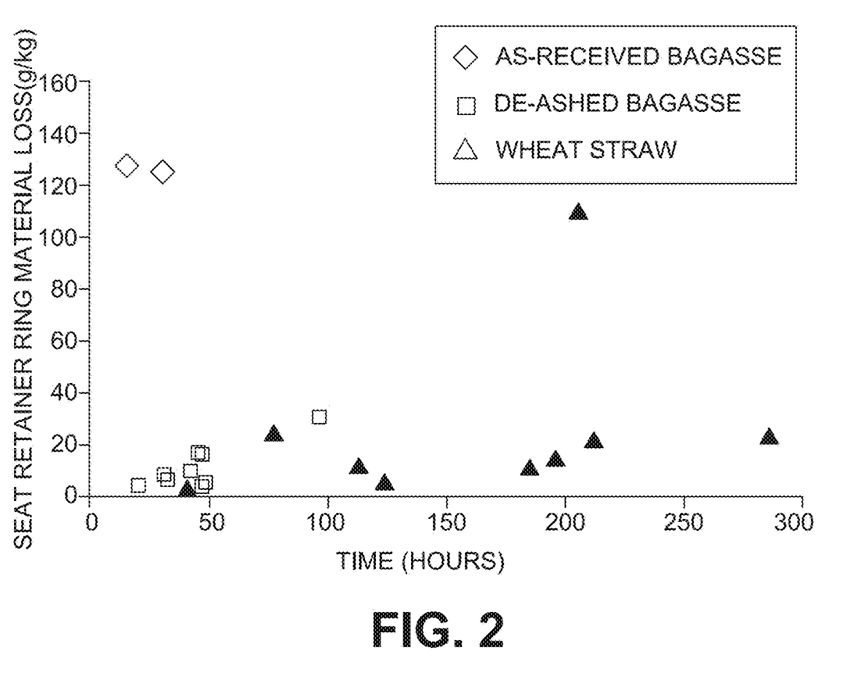
FIG. 2 shows seat retainer ring material loss (g/kg) of a blow valve as a function of time (hours) in service for as-received sugar cane bagasse, sieved bagasse and wheat straw.

The results of the material loss of wheat straw, de-ashed bagasse and bagasse not subjected to ash removal as a function of time in operation are shown in FIG. 2. As shown in FIG. 2, de-ashing of bagasse feedstock compared to bagasse without ash removal reduced the material loss of the seat retainer ring material significantly. The material loss of the ring for the de-ashed bagasse was reduced roughly 100× relative to the as-received bagasse feedstock (compare diamond data points to square data points of FIG. 2). The material loss on the blow valve component parts due to the bagasse that was not sieved was believed to be due to the high concentration of ash, particularly the silica component of the ash in the bagasse. The ash and silica of wheat straw, as-received bagasse and de-ashed bagasse is shown in Table 1 below.

TABLE 1

Ash and silica content in wheat straw, as-received bagasse and de-ashed bagasse

|  | As-received wheat straw | As-received bagasse | De-ashed bagasse |
| --- | --- | --- | --- |
| Silica (mg/g) | 24 ± 13 | 101 ± 29 | 21 ± 4 |
| Ash content (mg/g) | 52 ± 18 | 129 ± 36 | 34 ± 7 |

De-ashing reduced the silica content of bagasse to wheat straw levels (see Table 1 above). As shown in Table 1 above, the silica content of de-ashed bagasse was about 21 mg/g and as-received wheat straw was about 24 mg/g. The ash content of de-ashed bagasse was about 34 mg/g and as-received wheat straw was 52 mg/g. However, compared to wheat straw, the de-ashed bagasse was still more abrasive. The blow valve seat retainer ring material loss that was encountered after 200 hours of pretreatment time on wheat straw was observed after 50 hours on sieved bagasse at comparable feedstock throughput (see FIG. 2).

Example 5

Characterization of Bagasse Silica

In this example, the impact of silica particle size on erosion rates was examined. The particle size distribution for bagasse and wheat straw were obtained by laser diffraction using a Malvern Mastersizer™ 2000 instrument. The particles were subjected to the same ultrasound treatment and measurements were taken before and after such treatment. The particle size distribution for both bagasse and wheat straw are shown in FIGS. 3A and 3B.

Figure 3A:
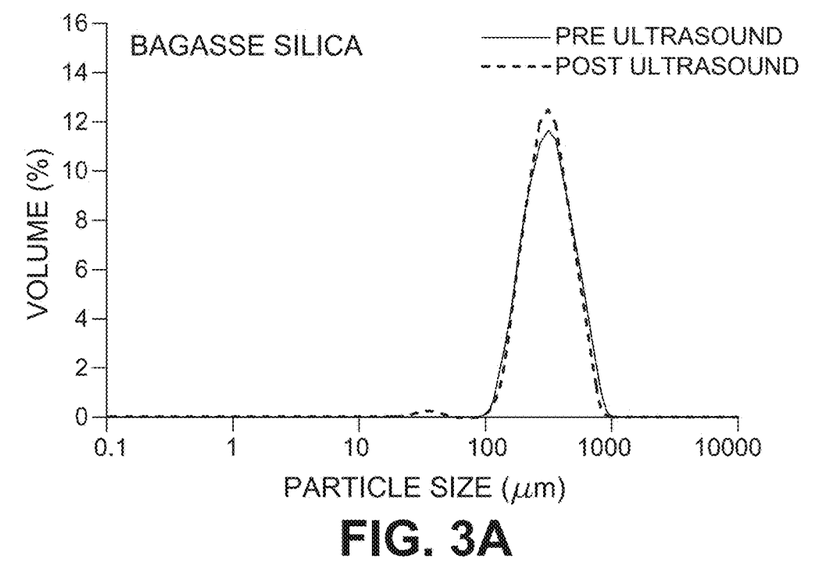
FIG. 3A shows volume (%) verses particle size (μm) of bagasse silica pre (solid line) and post (dotted line) ultrasound treatment.
Figure 3B:
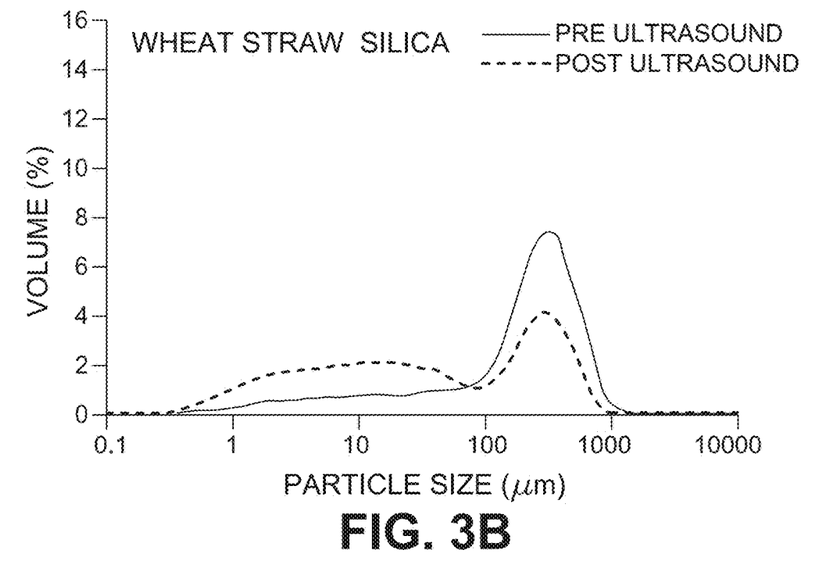
FIG. 3B shows volume (%) verses particle size (μm) of wheat straw silica pre (solid line) and post (dotted line) ultrasound treatment.

As seen by comparing FIGS. 3A and 3B, the bagasse silica particles were on average larger. The volume weighted mean particle size for bagasse particles was 313 μm compared to 116 μm for wheat straw. Ultrasound had only a small effect on bagasse silica but a significant impact on wheat straw silica. This is seen by comparing pre- and post-ultrasound data in FIGS. 3A and 3B. The volume percent of bagasse particles having a particles size of 313 μm remained essentially unchanged. By contrast, the volume percent of wheat straw silica particles having a particle size of 116 μm after ultrasound decreased more significantly.

This observation suggests that the wheat straw silica is either fractured or consists of agglomerates. The observation that bagasse silica was not impacted by ultrasound treatment suggests increased integrity of the silica particles compared to wheat straw silica particles.

Figure 4A:
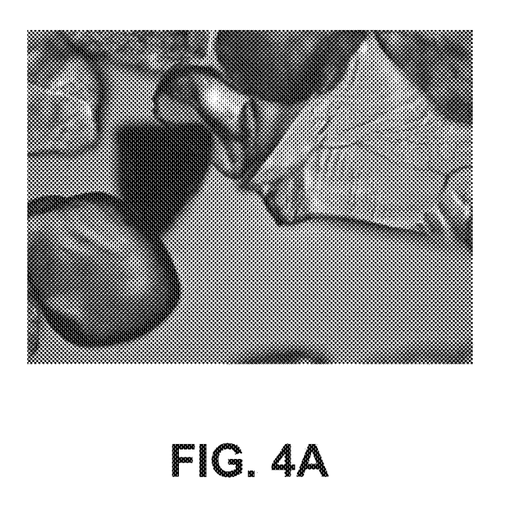
FIG. 4A is an optical microscope photograph of sugar cane bagasse silica.
Figure 4B:
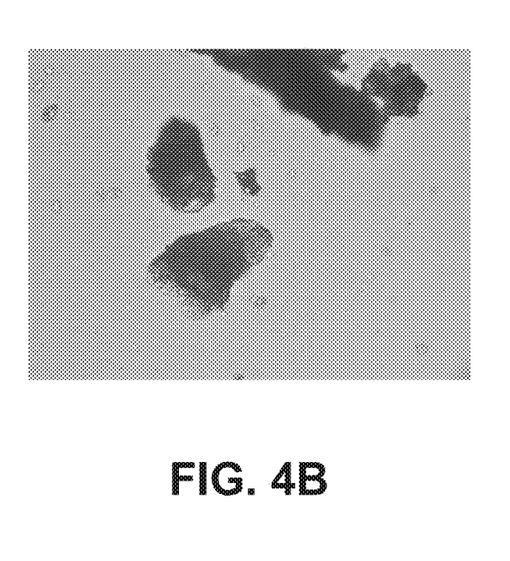
FIG. 4B is an optical microscope photograph of wheat straw silica.

The morphology of bagasse silica and wheat straw silica was subsequently examined by optical microscopy. Micrographs of sugar cane bagasse and wheat straw are shown in FIGS. 4A and 4B. The magnification of each sample is the same (40×). As shown by the micrographs, the surface area of the two silica samples is different. The bagasse silica has a single crystal appearance with smooth surfaces and sharp edges while the wheat straw silica is rounded and the grains appear to have an agglomerated structure.

Without being limited by theory, the micrographs suggest why ultrasound impacted the two silica samples differently. Ultrasound broke up the fractured and agglomerated wheat straw silica, while the solid bagasse silica was generally not affected. It is believed that the integrity and the morphology of the bagasse silica may be an explanation for the erosive properties of bagasse silica on the blow valve components.

It should be understood that the foregoing examples are for illustrative purposes only and should not be construed to limit the disclosed embodiments in any manner.

We claim:

1. A process for producing a fermentation product from a sugar cane derived cellulosic feedstock comprising:
   (i) subjecting the sugar cane derived cellulosic feedstock comprising bagasse, leaves, tops, or a combination thereof, to silica removal selected from processes comprising separating at least silica from the feedstock by size or density differences;
   (ii) pretreating the bagasse, leaves or tops, or a combination thereof, from which at least a portion of the silica has been removed under pressure to produce a pretreated feedstock;
   (iii) at least partially de-pressurizing the pretreated feedstock comprising passing the pretreated feedstock through an orifice, thereby producing a depressurized, pretreated feedstock;
   (iv) hydrolyzing the depressurized, pretreated feedstock with cellulase enzymes to produce glucose; and
   (v) fermenting the glucose to produce the fermentation product.

2. The process of claim 1, wherein the orifice is formed within a valve.

3. The process of claim 2, wherein the valve is a blow valve.

4. The process of claim 1, wherein the sugar cane derived cellulosic feedstock is at least partially de-watered after step (i) and before the step of pretreating.

5. The process of claim 1, wherein the pretreating comprises addition of an acid.

6. The process of claim 1, wherein inorganic salt, iron and/or alumina are removed from the sugar cane derived cellulosic feedstock in step (i).

7. A process for producing an alcohol from a sugar cane derived cellulosic feedstock comprising:
   (i) subjecting the sugar cane derived cellulosic feedstock comprising bagasse, leaves, tops, or a combination thereof, to silica removal selected from processes comprising sieving, screening, cyclone separation or any combination thereof, thereby removing at least silica therefrom;
   (ii) treating the bagasse, leaves or tops, or any combination thereof, from which at least a portion of the silica has been removed, in one or more processing stages to produce sugar, wherein the undissolved solids content of a slurry during said processing stages reaches a weight percent of at least 15%;
   (iii) fermenting the sugar to produce the alcohol with yeast or bacteria; and
   (iv) concentrating and recovering the alcohol.

8. A process for producing a fermentation product from a sugar cane derived cellulosic feedstock comprising:
   (i) subjecting the sugar cane derived cellulosic feedstock comprising bagasse, leaves, tops, or a combination thereof, to silica removal selected from processes comprising sieving, screening, cyclone separation or any combination thereof, thereby removing at least silica therefrom;
   (ii) treating the bagasse, leaves, tops, or any combination thereof, from which at least a portion of the silica has been removed, in one or more processing stages to produce sugar, wherein the undissolved solids content of a slurry during said processing stages is between 12 and 35 weight percent;
   (iii) fermenting the sugar to the fermentation product with yeast or bacteria; and
   (iv) recovering the fermentation product.

9. The process of claim 7, wherein the one or more processing stages comprise high consistency process equipment that comprises a dewatering device.

10. The process of claim 9, wherein the dewatering device is a screw press or plug screw.

11. The process of claim 7, wherein the one or more processing stages comprise pretreatment and wherein the silica is removed upstream of pretreatment.

12. The process of claim 7, wherein the bagasse, leaves, tops or any combination thereof, have an ash content of between 0.5 wt % and about 18 wt %.

13. The process of claim 12, wherein the ash content is between 5 wt % and 18 wt %.

14. The process of claim 7, wherein subjecting the sugar cane derived cellulosic feedstock comprising bagasse, leaves, tops, or a combination thereof, to silica removal comprises subjecting the bagasse, leaves, tops or any combination thereof to dry sieving or screening.

15. The process of claim 14, comprising drying the bagasse, leaves, tops or a combination thereof prior to dry sieving or screening.

16. The process of claim 7, wherein the bagasse, leaves, tops or any combination thereof are subjected to wet processing comprising removing silica by settling or by using at least one hydrocyclone.

17. The process of claim 7, wherein at least 20 weight percent of the silica from the bagasse, tops, leaves or any combination thereof is removed prior to step (ii).

18. The process of claim 7, wherein at least 40 weight percent of the silica from the bagasse, tops, leaves or any combination thereof is removed prior to step (ii).

19. The process of claim 7, wherein the one of more processing stages comprise soaking the bagasse, tops, leaves or any combination thereof in an aqueous solution.

20. The process of claim 19, wherein the aqueous solution comprises pretreatment chemical.

21. The process of claim 7, wherein the undissolved solids content of the slurry during said processing stages reaches a weight percent of at least 20%.

22. The process of claim 7, wherein the one or more processing stages comprise a step of pretreatment to produce pretreated feedstock and hydrolysis of cellulose contained in the pretreated feedstock with cellulase enzymes to produce the sugar.

23. A process for producing a fermentation product from a sugar cane derived cellulosic feedstock comprising:
(i) subjecting the sugar cane derived cellulosic feedstock comprising bagasse, leaves, tops, or a combination thereof, to silica removal selected from processes comprising sieving, screening, cyclone separation or any combination thereof, thereby removing at least silica therefrom;
(ii) treating the bagasse, leaves or tops, or any combination thereof, from which at least a portion of the silica has been removed, in one or more processing stages to produce sugar, wherein the undissolved solids content of a slurry fed to or formed during said one or more processing stages reaches a weight percent of at least 15%, and the processing stages comprise feeding a process stream to equipment susceptible to erosion, said equipment selected from a dewatering device, a heating chamber, a valve or a combination thereof; and
(iii) fermenting the sugar to produce a fermentation product.

24. The process of claim 23, wherein the equipment is a dewatering device.

25. The process of claim 23, wherein the equipment is a steam mixing device.

26. The process of claim 23, wherein the equipment is a blow valve.

27. The process of claim 23, wherein the fermentation product is ethanol and the ethanol is recovered to produce concentrated ethanol.

* * * * *